(12) United States Patent
Maile et al.

(10) Patent No.: US 7,844,334 B2
(45) Date of Patent: *Nov. 30, 2010

(54) DUAL-USE SENSOR FOR RATE RESPONSIVE PACING AND HEART SOUND MONITORING

(75) Inventors: Keith R. Maile, New Brighton, MN (US); Krzysztof Z. Siejko, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 443 days.

This patent is subject to a terminal disclaimer.

(21) Appl. No.: 11/778,527

(22) Filed: Jul. 16, 2007

(65) Prior Publication Data

US 2008/0015652 A1    Jan. 17, 2008

Related U.S. Application Data

(63) Continuation of application No. 10/703,175, filed on Nov. 6, 2003, now Pat. No. 7,248,923.

(51) Int. Cl.
*A61N 1/00* (2006.01)

(52) U.S. Cl. .............................. 607/18; 607/19; 600/528

(58) Field of Classification Search ................ 607/9–19, 607/62; 600/514, 528
See application file for complete search history.

(56) References Cited

U.S. PATENT DOCUMENTS

| 4,173,971 | A | 11/1979 | Karz |
| 4,291,699 | A | 9/1981 | Geddes et al. |
| 4,586,514 | A | 5/1986 | Schlager et al. |
| 4,702,253 | A | 10/1987 | Nappholz et al. |
| 4,796,639 | A | 1/1989 | Snow et al. |
| 4,830,006 | A | 5/1989 | Haluska et al. |
| 5,179,947 | A | 1/1993 | Meyerson et al. |
| 5,205,283 | A | 4/1993 | Olson |
| 5,305,745 | A | 4/1994 | Zacouto |
| 5,411,531 | A | 5/1995 | Hill et al. |
| 5,544,661 | A | 8/1996 | Davis et al. |

(Continued)

FOREIGN PATENT DOCUMENTS

EP    1179317 A2    2/2002

(Continued)

OTHER PUBLICATIONS

"U.S. Appl. No. 10/703,175, Non-Final Office Action mailed May 10, 2006", 7 pgs.

(Continued)

*Primary Examiner*—Scott M Getzow
(74) *Attorney, Agent, or Firm*—Schwegman, Lundberg & Woessner, P.A.

(57) ABSTRACT

An implantable medical device includes a dual-use sensor such as a single accelerometer that senses an acceleration signal. A sensor processing circuit processes the acceleration signal to produce an activity level signal and a heart sound signal. The implantable medical device provides for rate responsive pacing in which at least one pacing parameter, such as the pacing interval, is dynamically adjusted based on the physical activity level. The implantable medical device also uses the heart sounds for pacing control purposes or transmits a heart sound signal to an external system for pacing control and/or diagnostic purposes.

20 Claims, 6 Drawing Sheets

U.S. PATENT DOCUMENTS

| | | | |
|---|---|---|---|
| 5,554,177 | A | 9/1996 | Kieval et al. |
| 5,792,195 | A * | 8/1998 | Carlson et al. .................. 607/17 |
| 5,935,081 | A | 8/1999 | Kadhiresan |
| 5,951,593 | A | 9/1999 | Lu et al. |
| 6,002,777 | A | 12/1999 | Grasfield et al. |
| 6,048,319 | A | 4/2000 | Hudgins et al. |
| 6,058,329 | A | 5/2000 | Salo et al. |
| 6,076,015 | A | 6/2000 | Hartley et al. |
| 6,208,900 | B1 | 3/2001 | Ecker et al. |
| 6,272,377 | B1 | 8/2001 | Sweeney et al. |
| 6,477,406 | B1 | 11/2002 | Turcott |
| 6,480,733 | B1 | 11/2002 | Turcott |
| 6,542,775 | B2 | 4/2003 | Ding et al. |
| 6,643,548 | B1 | 11/2003 | Mai et al. |
| 6,684,103 | B2 | 1/2004 | Ding et al. |
| 6,792,308 | B2 | 9/2004 | Corbucci |
| 6,804,558 | B2 | 10/2004 | Haller et al. |
| 6,885,889 | B2 | 4/2005 | Chinchoy |
| 6,942,622 | B1 | 9/2005 | Turcott |
| 7,115,096 | B2 | 10/2006 | Siejko et al. |
| 7,123,962 | B2 | 10/2006 | Siejko et al. |
| 7,139,609 | B1 * | 11/2006 | Min et al. ....................... 607/17 |
| 7,194,306 | B1 | 3/2007 | Turcott |
| 7,226,422 | B2 | 6/2007 | Hatlestad et al. |
| 7,248,923 | B2 | 7/2007 | Maile et al. |
| 7,424,321 | B2 | 9/2008 | Wariar et al. |
| 7,480,528 | B2 | 1/2009 | Brockway et al. |
| 7,662,104 | B2 | 2/2010 | Siejko et al. |
| 2002/0072684 | A1 | 6/2002 | Stearns |
| 2002/0091415 | A1 | 7/2002 | Lovett et al. |
| 2002/0128563 | A1 | 9/2002 | Carlson et al. |
| 2002/0151812 | A1 | 10/2002 | Scheiner et al. |
| 2002/0151938 | A1 | 10/2002 | Corbucci |
| 2003/0014083 | A1 | 1/2003 | Kupper |
| 2003/0105497 | A1 | 6/2003 | Zhu et al. |
| 2003/0144702 | A1 | 7/2003 | Yu et al. |
| 2003/0144703 | A1 | 7/2003 | Yu et al. |
| 2003/0208240 | A1 | 11/2003 | Pastore et al. |
| 2003/0233132 | A1 | 12/2003 | Pastore et al. |
| 2004/0039295 | A1 | 2/2004 | Olbrich et al. |
| 2004/0073093 | A1 | 4/2004 | Hatlestad |
| 2004/0102712 | A1 | 5/2004 | Belalcazar et al. |
| 2004/0106960 | A1 | 6/2004 | Siejko et al. |
| 2004/0106961 | A1 | 6/2004 | Siejko et al. |
| 2004/0127792 | A1 | 7/2004 | Siejko et al. |
| 2004/0176810 | A1 | 9/2004 | Stadler et al. |
| 2004/0215265 | A1 | 10/2004 | Keizer |
| 2005/0004485 | A1 | 1/2005 | Crosby et al. |
| 2005/0065448 | A1 | 3/2005 | Stahmann et al. |
| 2005/0065556 | A1 | 3/2005 | Reghabi et al. |
| 2005/0102001 | A1 | 5/2005 | Maile et al. |
| 2005/0137631 | A1 | 6/2005 | Yu et al. |
| 2005/0148896 | A1 | 7/2005 | Siejko et al. |
| 2005/0256542 | A1 | 11/2005 | Pastore et al. |
| 2006/0020294 | A1 | 1/2006 | Brockway et al. |
| 2006/0020295 | A1 | 1/2006 | Brockway et al. |
| 2006/0025699 | A1 | 2/2006 | Maile et al. |
| 2006/0030892 | A1 | 2/2006 | Kadhiresan et al. |
| 2006/0161070 | A1 | 7/2006 | Siejko et al. |
| 2006/0167518 | A1 | 7/2006 | Gill et al. |
| 2006/0270939 | A1 | 11/2006 | Wariar et al. |
| 2006/0282000 | A1 | 12/2006 | Zhang et al. |
| 2007/0078491 | A1 | 4/2007 | Siejko et al. |
| 2007/0149890 | A1 | 6/2007 | Li et al. |
| 2007/0162081 | A1 | 7/2007 | Yu et al. |
| 2007/0239218 | A1 | 10/2007 | Carlson et al. |
| 2007/0299356 | A1 | 12/2007 | Wariar et al. |
| 2008/0177191 | A1 | 7/2008 | Patangay et al. |
| 2009/0132000 | A1 | 5/2009 | Brockway et al. |
| 2009/0287106 | A1 | 11/2009 | Zhang et al. |
| 2010/0099997 | A1 | 4/2010 | Siejko et al. |

FOREIGN PATENT DOCUMENTS

| | | | |
|---|---|---|---|
| EP | 1247485 | A1 | 10/2002 |
| JP | 61202653 | | 9/1986 |
| JP | 63-109103 | U | 7/1988 |
| JP | 63-290544 | A | 11/1988 |
| JP | 06-277189 | A | 10/1994 |
| JP | 2000-060846 | A | 2/2000 |
| JP | 2000316825 | | 11/2000 |
| WO | WO-01/56651 | A1 | 8/2001 |
| WO | WO-2004/012815 | A1 | 2/2004 |
| WO | WO-2004/050178 | A1 | 6/2004 |
| WO | WO-2007/126578 | A2 | 11/2007 |

OTHER PUBLICATIONS

"U.S. Appl. No. 10/703,175, Notice of Allowance mailed Mar. 19, 2007", 5 pgs.

"U.S. Appl. No. 10/703,175, Response filed Aug. 9, 2006 to Non-Final Office Action mailed May 10, 2006", 20 pgs.

"U.S. Appl. No. 10/703,175, Response filed Dec. 12, 2006 to Final Office Action mailed Oct. 12, 2006", 21 pgs.

"U.S. Appl. No. 10/703,175, Final Office Action mailed Oct. 12, 2006", 8 pgs.

Aaron, S. D, et al., "How Accurate is Spirometry at Predicting Restrictive Pulmonary Impairment?", *Chest*,115(3), (Mar. 1999), 869-873.

Breithardt, O. A., et al., "Acute Effects of Cardiac Resynchronization Therapy on Functional Mitral Regurgitation in Advanced Systolic Heart Failure", *Journal of the American College of Cardiology*, 41(5), (May 21, 2003), 765-770.

Carabello, B. A., "Mitral valve disease", *Current Problems in Cardiology*, 18(7), (Jul. 1993), 423-478.

Fenster, M. S., et al., "Mitral Regurgitation: An Overview", *Curr Probl Cardiol.*, 20(4), (Apr. 1995), 193-280.

Kinderman, M., et al., "Optimizing the AV Delay in DDD Pacemaker Patients with High Degree AV Block: Mitral Valve Doppler Versus Impedance Cardiography", *PACE*, 20(Part I), (Oct. 1997), 2453-2462.

Leonelli, F. M, et al., "Systolic and Diastolic Effects of Variable Atroventricular Delay and Patients with Complete Hear Block and Normal Ventricular Function", *Amer. J-Cardiology*, vol. 80, (Aug. 1, 1997), 294-298.

Prinzen, F. W, "Mapping of regional myocardial strain and work during ventricular pacing: experimental study using magnetic resonance imaging tagging", *Journal of the American College of Cardiology*, 33(6), (May 1999), 1735-1742.

Ritter, P., et al., "New Method for Determining the Optimal Atrio-Ventricular Delay in Patients Place in DDD Mode for Complete Atrio-Ventricular Block", *NASPE* (Abstract #237), (1995), p. 885.

Rosa, A., et al., "Ectopic Pacing at Physiological Rate Improves Postanoxic Recovery of the Developing Heart", *Am. J. Physiol.—Heart Circ. Physiol., 284*, (2003), H2384-H2392.

Say, O., et al., "Classification of heart sounds by using wavelet transform", *24th Annual Conference and the Annual Fall Meeting of the Biomedical Engineering Society, EMBS/BMES Conference*, vol. 1, (2002), 128-129.

Zin, Z. M, et al., "Wavelet analysis and classification of mitral regurgitation and normal heart sounds based on artificial neural networks", *Seventh International Symposium on Signal Processing and Its Applications*, vol. 2, (Jul. 1-4, 2003), 619-620.

\* cited by examiner

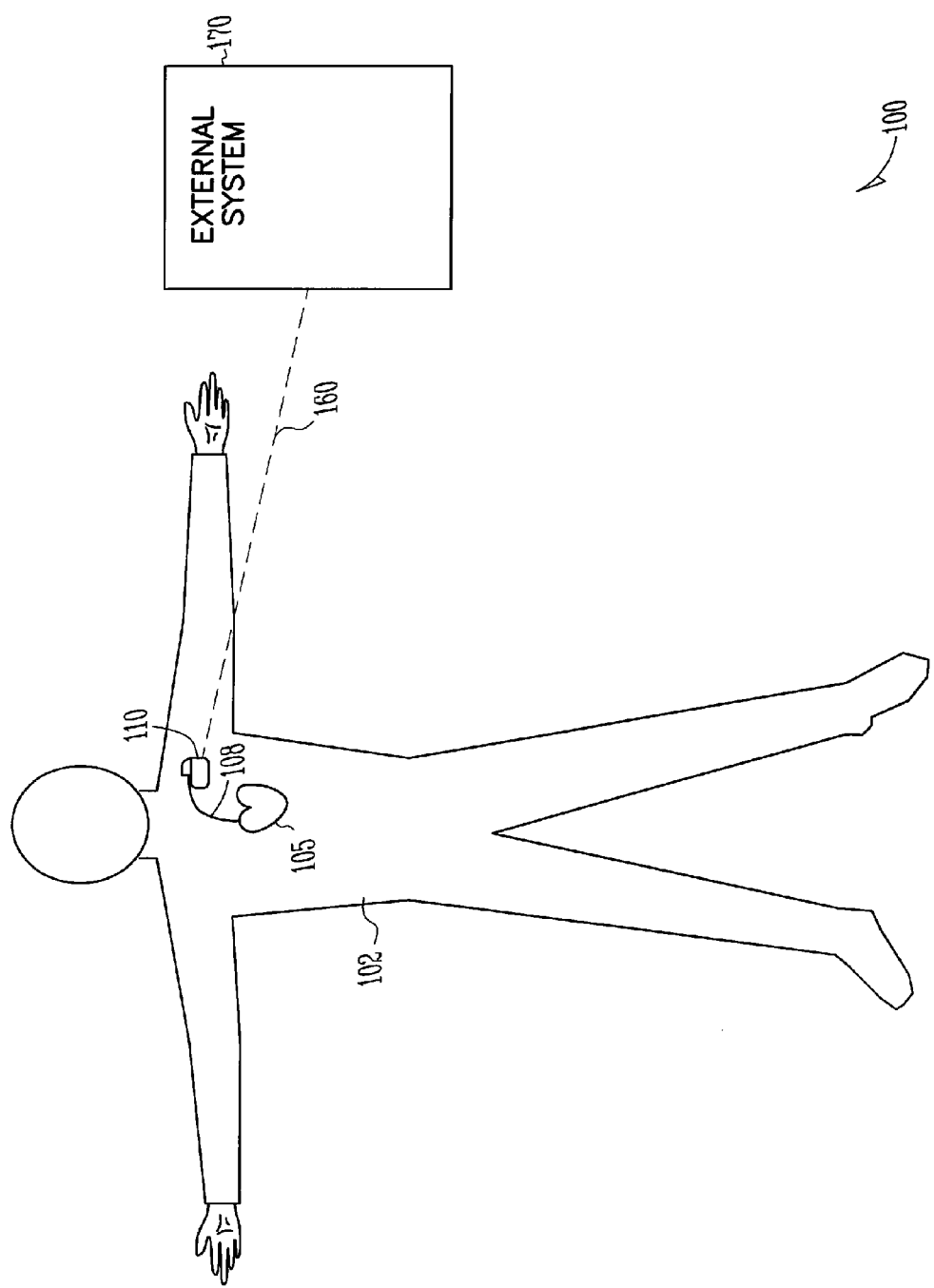

DUAL-USE SENSOR FOR RATE RESPONSIVE PACING AND HEART SOUND MONITORING

CROSS-REFERENCE TO RELATED APPLICATIONS

This application is a continuation of U.S. patent application Ser. No. 10/703,175, filed on Nov. 6, 2003, now U.S. Pat. No. 7,248,923 the specification of which is incorporated herein by reference.

This application is related to commonly assigned U.S. patent application Ser. No. 10/307,896, entitled "PHONOCARDIOGRAPHIC IMAGE-BASED ATRIOVENTRICULAR DELAY OPTIMIZATION," filed on Dec. 2, 2002, and U.S. patent application Ser. No. 10/334,694, entitled "METHOD AND APPARATUS FOR MONITORING OF DIASTOLIC HEMODYNAMICS," filed on Dec. 30, 2002, which are hereby incorporated by reference.

TECHNICAL FIELD

This document relates generally to cardiac rhythm management systems and particularly, but not by way of limitation, to such a system sensing heart sounds and delivering rate responsive pacing.

BACKGROUND

A heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the organs and pump it into the lungs where the blood gets oxygenated. The body's metabolic need for oxygen increases with the body's physical activity level. The pumping functions are accomplished by contractions of the myocardium (heart muscles). An increase in the body's metabolic need for oxygen is satisfied primarily by a higher frequency of the contractions, i.e., a higher heart rate. In a normal heart, the sinoatrial node, the heart's natural pacemaker, generates electrical impulses, called action potentials, that propagate through an electrical conduction system to various regions of the heart to excite myocardial tissues in these regions. Coordinated delays in the propagations of the action potentials in a normal electrical conduction system cause the various regions of the heart to contract in synchrony such that the pumping functions are performed efficiently.

The functions of the sinoatrial node and the electrical conduction system are indicated by electrocardiography (ECG) with at least two electrodes placed in or about the heart to sense the action potentials. When the heart contracts irregularly or otherwise abnormally, one or more ECG signals indicate that contractions at various cardiac regions are chaotic and unsynchronized. Such conditions are known as cardiac arrhythmias. Cardiac arrhythmias result in a reduced pumping efficiency of the heart, and hence, diminished blood circulation.

Pacing therapy treats cardiac arrhythmias by using an implantable pacemaker to deliver electrical pulses that substitute for the action potentials to excite the myocardium, thereby restoring the functions of the sinoatrial note and/or the natural electrical conduction system. To ensure that the body receives sufficient oxygen to satisfy its metabolic needs, a pacing mode referred to as rate responsive pacing, or rate adaptive pacing, uses an indication of the body's physical activity level to dynamically adjust the pacing rate, which determines the frequency of the contractions.

Various mechanical functions of the heart, as well as electro-mechanical association between the electrical conduction system and the myocardium, are indicated by heart sounds. For example, amplitudes of the third heart sound (S3) and fourth heart sound (S4) are related to filing pressures of the left ventricle during diastole. Fundamental frequencies of S3 and S4 are related to ventricular stiffness and dimension. Chronic changes in S3 amplitude is correlated to left ventricular chamber stiffness and degree of restrictive filling. Change in the interval between atrial contraction and S4 is correlated to the changes in left ventricular end of diastolic pressure. Such parameters, being correlated to the heart's mechanical properties and electromechanical association, quantitatively indicate abnormal cardiac conditions such as heart failure, including degrees of severity, and need of appropriate therapies.

For these and other reasons, there is a need for an implantable pacemaker that senses the body's physical activity level and the heart sounds. Implantability requires that any circuit or functional module of the implantable pacemaker to be designed for the minimum size and energy consumption.

SUMMARY

An implantable medical device includes a dual-use sensor such as a single accelerometer that senses an acceleration signal. A sensor processing circuit processes the acceleration signal to produce an activity level signal and a heart sound signal. The implantable medical device provides for rate responsive pacing in which at least one pacing parameter, such as the pacing interval, is dynamically adjusted based on the physical activity level. The implantable medical device also uses the heart sounds for pacing control purposes or transmits a heart sound signal to an external system for pacing control and/or diagnostic purposes.

In one embodiment, a cardiac rhythm management system includes a sensing circuit, a pacing circuit, a dual-use sensor, a sensor processing circuit, and a controller. The sensing circuit senses at least one electrogram. The pacing circuit delivers pacing pulses. The dual-use sensor senses a signal indicative of activities and heart sounds. The sensor processing circuit produces an activity level signal and a heart sound signal from the sensed signal. The controller includes a rate responsive pacing algorithm execution module dynamically adjusting at least a pacing interval based on at least the activity level signal.

In one embodiment, a cardiac rhythm management system includes an accelerometer, a processing circuit, and a controller. The accelerometer senses an acceleration signal indicative of physical activities and heart sounds. The processing circuit has an input to receive the acceleration signal, an amplifier, and a band-pass filter. The amplifier has a programmable gain. The band-pass filter has one or more cutoff frequencies programmable for producing an activity level signal during first time periods and producing a heart sound signal during second time periods. The controller includes a processing circuit programming module adapted to program the gain and the cutoff frequencies.

In one embodiment, a cardiac rhythm management system includes an accelerometer to sense an acceleration signal, a first processing circuit, and a second processing circuit. The first processing circuit includes a first input to receive the acceleration signal, a first output indicative of a physical activity level, and a first gain-and-filter circuit to provide for a first gain and a first set of cutoff frequencies. The second processing circuit includes a second input to receive the acceleration signal, a second output indicative of heart sounds, and a second gain-and-filter circuit to provide for a second gain and a second set of cutoff frequencies.

In one embodiment, a signal indicative of activities and heart sounds is sensed using a single implantable sensor. The sensed signal is processed to produce an activity level signal and a heart sound signal. A rate responsive pacing algorithm dynamically adjusts at least one pacing parameter based on the activity level signal. At least one type of heart sounds is detected from the heart sound signal.

In one embodiment, an acceleration signal indicative of an activity level and heart sounds is sensed. An amplifier is programmed with a first gain suitable for sensing the activity level for a first time period. A band-pass filter is programmed with a first set of cutoff frequencies suitable for sensing the activity level for the first time period. The sensed acceleration signal is amplified and filtered to produce an activity level signal. The amplifier is programmed with a second gain suitable for sensing the heart sounds for a second time period. The band-pass filter is programmed with a second set of cutoff frequencies suitable for sensing the heart sounds for the second time period. The sensed acceleration signal is amplified and filtered to produce a heart sound signal.

In one embodiment, an acceleration signal is sensed. An activity level signal and a heart sound signal is produced concurrently from the acceleration signal by amplifying and filtering. The acceleration signal is amplified with a first gain and filtered with a first set of cutoff frequencies suitable for producing the activity level signal, and is amplified with a second gain and filtered with a second set of cutoff frequencies suitable for producing the heart sound signal.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document.

FIG. 1 is a block diagram illustrating an embodiment of a cardiac rhythm management system, including an implantable medical device, and portions of an environment in which it is used.

DETAILED DESCRIPTION

Figure 2A:
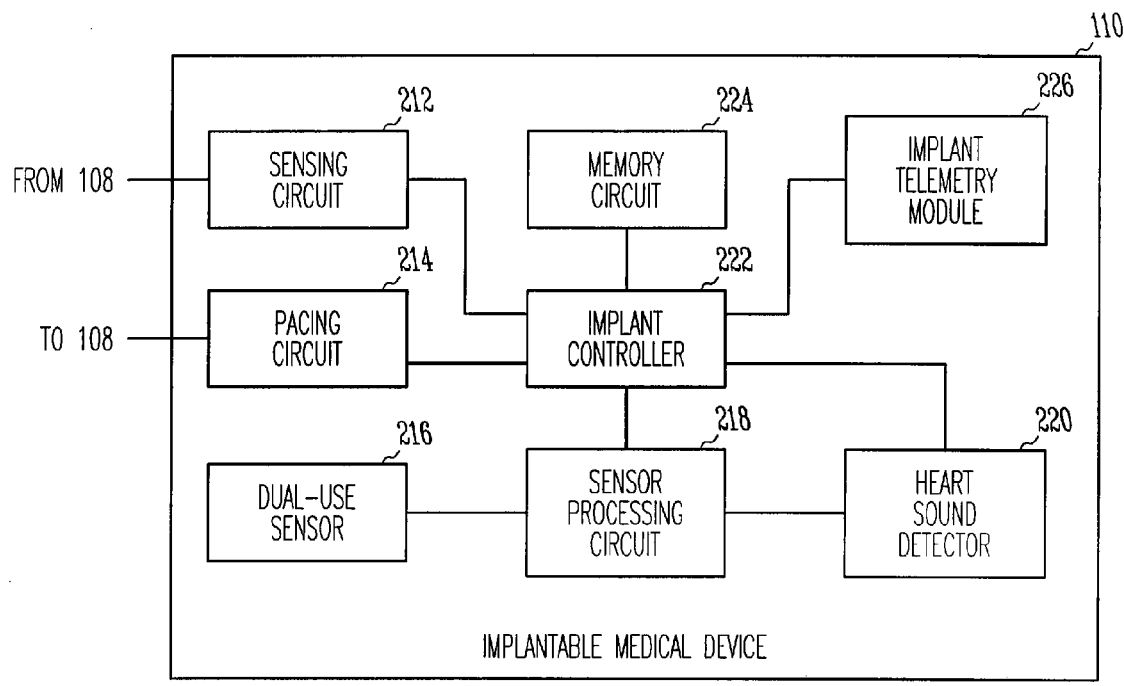
FIG. 2A is a block diagram illustrating an embodiment of a circuit of the implantable medical device.

In the following detailed description, reference is made to the accompanying drawings which form a part hereof, and in which is shown by way of illustration specific embodiments in which the invention may be practiced. These embodiments are discussed in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document discusses, among other things, a cardiac rhythm management system including a dual-use sensor, such as a single accelerometer, for rate responsive pacing and heart sound sensing. The cardiac rhythm management system includes, for example, an implantable medical device including such as a pacemaker, a pacemaker/defibrillator, a pacemaker/drug delivery device, or a cardiac resynchronization therapy (CRT) device. The implantable medical device provides for rate responsive pacing and heart sound sensing.

Rate response pacing, also referred to as rate adaptive pacing, uses an indication of a patient's gross physical activity level to adjust a pacing rate, such that the cardiac output as a result of pacing meets or approaches the patient's metabolic need. One example of rate responsive pacing using acceleration to adjust the pacing rate is discussed in U.S. Pat. No. 5,179,947, entitled "ACCELERATION-SENSITIVE CARDIAC PACEMAKER AND METHOD OF OPERATION," assigned to Cardiac Pacemakers, Inc., which is hereby incorporated by reference in its entirety.

Known and studied heart sounds include the "first heart sound," or S1, the "second heart sound," or S2, the "third heart sound," or S3, the "fourth heart sound," or S4, and their various sub-components. S1 is known to be indicative of, among other things, mitral valve closure, tricuspid valve closure, and aortic valve opening. S2 is known to be indicative of, among other things, aortic valve closure and pulmonary valve closure. S3 is known to be a ventricular diastolic filling sound often indicative of certain pathological conditions including heart failure. S4 is known to be a ventricular diastolic filling sound resulted from atrial contraction and is usually indicative of pathological conditions. The term "heart sound" hereinafter refers to any heart sound (e.g., S1) and any components thereof (e.g., M1 component of S1, indicative of Mitral valve closure and Mitral regurgitation). Heart sounds are used, for example, to calculate pacing parameters for improving the patient's hemodynamic performance and diagnosing a pathological condition such as heart failure. Examples of such uses are discussed in U.S. patent application Ser. No. 10/307,896, entitled "PHONOCARDIO-GRAPHIC IMAGE-BASED ATRIOVENTRICULAR DELAY OPTIMIZATION," and U.S. patent application Ser. No. 10/334,694, entitled "METHOD AND APPARATUS FOR MONITORING OF DIASTOLIC HEMODYNAMICS," both assigned to Cardiac Pacemakers, Inc., the specifications of which are incorporated herein by reference in their entirety.

An accelerometer can be used to sense both the physical activity level for rate responsive pacing and the heart sounds because the two signals feature substantially distinguishable spectrums. The acceleration measured in the direction normal to a person's chest wall is indicative of both the physical activity level and the heart sounds. The sensor specifications required for sensing the physical activity level and the sensor specifications required for sensing the heart sounds, such as bandwidth, sensitivity, noise floor, robustness, size, and power consumption are sufficiently close such that they can be satisfied by a single accelerometer having adequate size and power consumption for used in an implantable medical device. A sensor processing circuit processes the signal sensed by such an accelerometer to produce an activity level signal indicative of the physical activity level for rate responsive pacing and a heart sound signal from which heart sounds of each type can be detected.

Throughout this document, a "heart sound signal" includes audible and inaudible mechanical vibrations of the heart that can be sensed with a sensor such as an accelerometer. A "heart sound" refers to a recognized event in the heart sound signal. Unless noted otherwise, S1, S2, S3, and S4 refer to the first, second, third, and fourth heart sounds, respectively, as a heart sound type, or as one or more occurrences of the corresponding type heart sounds, depending on the context. An "electrogram" includes an electrocardiogram (ECG) sensed with at least an intracardiac electrode placed in the heart or an epicardial electrode placed on the heart. A "user" includes a physician or other caregiver who examines and/or treats a patient using one or more of the methods and apparatuses discussed in the present document.

FIG. 1 is a block diagram illustrating an embodiment of a cardiac rhythm management system 100, and portions of an environment in which it is used. System 100 includes an implantable medical device 110, a lead system 108, an external system 170, and a wireless telemetry link 160.

After implantation, implantable medical device 110 operates within a body 102 to sense activities of a heart 105 and deliver one or more therapies to heart 105. Implantable medical device 110 includes a pacemaker capable of rate responsive pacing. In one embodiment, implantable medical device 110 is an implantable pacemaker. In another embodiment, implantable medical device 110 includes a pacemaker module and one or more other therapeutic modules, such as a cardioversion-defibrillation module and a drug delivery module. In one specific embodiment, the pacemaker includes a cardiac resynchronization therapy module capable of delivering multi-site biventricular pacing. Implantable medical device 110 senses an activity level for rate responsive pacing purposes and heart sounds for various diagnostic and/or therapy control purposes. A dual-use sensor such as an accelerometer is used for sensing both the activity level and the heart sounds. In one embodiment, the dual-use sensor is within implantable medical device 110.

Lead system 108 provides one or more electrical connections between implantable medical device 110 and heart 105. It includes one ore more pacing leads each having one or more electrodes for electrogram sensing and pacing pulse delivery. In one embodiment, the dual-use sensor is incorporated into a lead of lead system 108 and connected to implantable medical device through the lead.

External system 170 communicates with implantable medical device 110. It allows a user and/or a patient to communicate and/or to control the operation of implantable medical device 110. In one embodiment, external system 170 includes an external programmer. In another embodiment, external system 170 includes an advanced patient management system, such as discussed in U.S. patent application Ser. No. 10/323,604, entitled "ADVANCED PATIENT MANAGEMENT FOR DEFINING, IDENTIFYING AND USING PREDETERMINED HEALTH-RELATED EVENTS," assigned to Cardiac Pacemakers, Inc., the specification of which is incorporated herein by reference in its entirety. The advanced patient management system allows the user to access implantable medical device 110 from a remote location.

Telemetry link 160 provides for data transmissions between implantable medical device 110 and external system 170. In one embodiment, telemetry link 160 is an inductive telemetry link. In an alternative embodiment, telemetry link 160 is a far-field radio-frequency telemetry link. Telemetry link 160 provides for data transmission from implantable medical device 110 to external system 170. This may include, for example, transmitting real-time physiological data acquired by implantable medical device 110, extracting physiological data acquired by and stored in implantable medical device 110, extracting therapy history data stored in implantable medical device 110, and extracting data indicating an operational status of implantable medical device 110 (e.g., battery status and lead impedance). Telemetry link 160 also provides for data transmission from external system 170 to implantable medical device 110. This may include, for example, programming implantable medical device 110 to acquire physiological data, programming implantable medical device 110 to perform at least one self-diagnostic test (such as for a battery status and lead impedance status), and programming implantable medical device 110 to deliver at least one therapy. Examples of signals represented by the physiological data include, but are not limited to, electrograms, heart sounds or signals indicative of heart sounds, activity level signals, and respiratory signals. In one embodiment, the physiological data also include parameters measured from one or more of these signals. In one embodiment, external system 170 or a user determines and/or adjusts a therapy based on these signals and/or physiological data.

FIG. 2A is a block diagram illustrating an embodiment of a circuit of implantable medical device 110. Implantable medical device 110 includes a sensing circuit 212, a pacing circuit 214, a dual-use sensor 216, a sensor processing circuit 218, a heart sound detector 220, an implant controller 222, a memory circuit 224, and an implant telemetry module 226. In one embodiment, these circuit elements, and possibly additional circuit elements of implantable medical device 110, are encapsulated in a hermetically sealed implantable housing. In another embodiment, some of these circuit elements, such as dual-use sensor 216 or implant telemetry module 224, are located outside of the hermetically sealed implantable housing.

Sensing circuit 212 and pacing circuit 214 are both electrically coupled to heart 105 via lead system 108. Sensing circuit 212 includes an amplifier circuit suitable for sensing one or more electrograms from heart 108 through lead system 108. Pacing circuit 214 includes a pulse generator generating electrical pacing pulses that are delivered to heart 105 through lead system 108.

Dual-use sensor 216 senses a signal indicative of two activities, events, or quantities having distinguishable frequency characteristics. The term "dual-use" refers to the fact that the two activities, events, or quantities are extracted separately from the signal and used for different purposes serving the functions of system 100. In one embodiment, dual-use sensor 216 includes a single accelerometer that senses an acceleration signal indicative of a patient's gross physical activity level and heart sounds of the patient. In one embodiment, dual-use sensor 216 is an integrated circuit accelerometer. A specific example of such an integrated circuit accelerometer is a piezoelectric accelerometer made by Endevco Corporation (Model 12 Picochip Accelerometer). Other examples include piezoresistive and capacitive accelerometers. In one embodiment, dual-use sensor 216 is encapsulated in the hermetically sealed implantable housing. This embodiment provides the accelerometer with an environment ensuring a stable operation. In an alternative embodiment, dual-use sensor 216 is incorporated into a lead of lead system 108. This embodiment allows the accelerometer to be located in or near heart 105, thus being more sensitive to the heart's mechanical activities such as vibrations (heart sounds).

Sensor processing circuit 218 processes the acceleration signal to produce an activity level signal indicative of the patient's gross physical activity level and a heart sound signal indicative of the patient's heart sounds. Embodiments of sensor processing circuit 218 are discussed below, with reference to FIGS. 3-5.

In one embodiment, heart sound detector 220 detects heart sounds from the heart sound signal produced by sensor processing circuit 218. In one embodiment, implantable controller 222 receives the detected heart sounds use it, in addition to the activity level signal, for rate responsive pacing purposes. In a further or alternative embodiment, implantable controller 222 uses the detected heart sounds for adjusting atrioventricular and/or interventricular pacing delays, such as in a cardiac resynchronization therapy for heart failure. The detected heart sounds, and/or parameters measured from the detected heart sounds, are also transmitted to external system 170 through telemetry link 160 for further analysis by the system or the user. In an alternative embodiment, the heart sound signal is transmitted to external system 170 though telemetry link 160. External system 170 detects and analyzes the heart sound signal for diagnostic and/or pacing control purposes. Heart sound detector 220 is configured and/or programmed by external system 170 to detect one or more of the S1, S2, S3, and S4 type heart sounds.

Implant controller 222 controls the operation of the entire implantable medical device 110. An embodiment of implantable device 222 is discussed below, with reference to FIG. 2B. In one embodiment, implant controller 222 is implemented using a microprocessor. Memory circuit 224 provides a storage medium for a device control code, parameters for the operation of implantable medical device 110, and the data acquired by implantable medical device 110. In one embodiment, memory circuit 224 includes a buffer for storing the signal sensed by dual-use sensor 216, the activity level signal produced by sensor processing circuit 218, and/or the heart sound signal produced by sensor processing circuit 218. In another embodiment, the buffer also stores the one or more electrograms sensed by sensing circuit 212. In a further embodiment, implant controller 222 includes an event detector to detect cardiac events and a maker generator to generate event markers representing the cardiac events. Examples of such cardiac events include sensed events (intrinsic depolarizations) and paced events (paced contractions or pulse deliveries) associated with one or more cardiac sites. Each event mark is indicative of the type and the timing of one cardiac event. In this embodiment, the buffer further stores the event markers. In one embodiment, the activity level signal and/or the heart sound signal are synchronized with the event markers such that the event markers serve as a timing reference relating the activity level and/or heart sound to the cardiac events. In one embodiment, implant controller 222 includes an analog-to-digital converter to digitize one or more of the signal sensed by dual-use sensor 216, the activity level signal, the heart sound signal, and the electrograms for storage and/or further processing. The analog-to-digital converter has a programmable sampling rate. Implantable controller 222 includes a digitization control module to control this sampling rate. In one embodiment, the sampling rate is programmable through external system 170.

Implant telemetry module 226 includes an antenna and a transceiver to support two-way communications with external system 170 via telemetry link 160. In one embodiment, one or more of the electrograms, the event markers, the signal sensed by dual-use sensor 216, the activity level signal, and the heart sound signal are transmitted to external system 170 in real time. In another embodiment, one or more of the electrograms, the event markers, the signal sensed by dual-use sensor 216, the activity level signal, and the heart sound signal are stored in the buffer of memory circuit 224 and retrieved from the buffer when needed. In one embodiment, the retrieval occurs at predetermined times as controlled by implant controller 222. In another embodiment, the retrieval occurs in response to a command from external system 170.

Figure 2B:
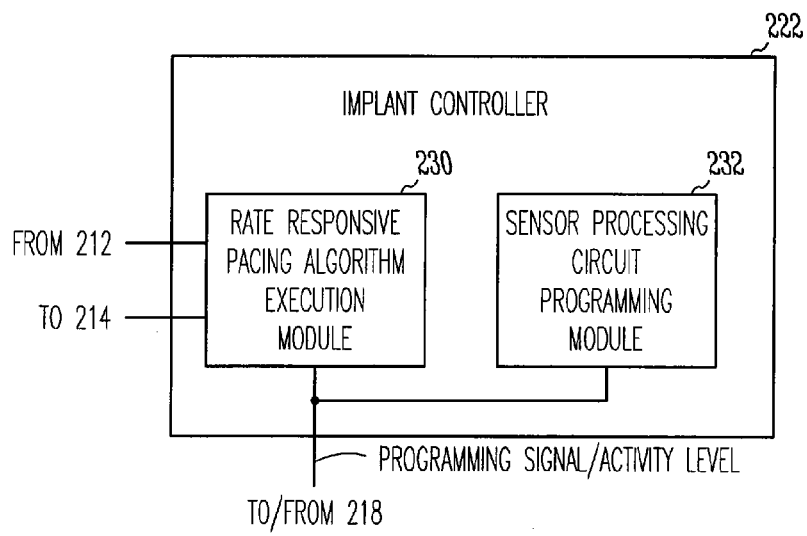
FIG. 2B is a block diagram illustrating an embodiment of a controller being a part of the circuit of the implantable medical device.

FIG. 2B is a block diagram illustrating an embodiment of implant controller 222. Implant controller 222 executes the device control code stored in memory circuit 224. It includes, among other control modules, a rate responsive pacing algorithm execution module 230 and a sensor processing circuit programming module 232.

Rate responsive pacing algorithm execution module 230 controls the timing of the pacing pulse delivery from pacing circuit 214, based on predefined pacing logic and timing rules and one or more of the activity level signal, the sensed electrograms, timing of previous pacing pulse deliveries, the detected heart sounds, and possibly other physiological signals indicative of electrical events, mechanical activities, and/or hemodynamic performance of heart 105. It includes a pacing interval calculator to calculate a pacing interval based on at least the activity level signal and predetermined maximum and minimum pacing intervals. When the pacing interval calculator produces a new value for the pacing interval, rate responsive pacing algorithm execution module 230 updates the pacing interval with the new value. In one embodiment, rate responsive pacing algorithm execution module 230 performs the calculation and the update dynamically, for each and every heart beat.

In one embodiment, sensor processing circuit programming module 232 controls the timing, gain, and/or frequency responses of sensor processing circuit 218 to produce the activity level signal and the heart sound signal. The programming of sensor processing circuit 218 is discussed below with reference to FIGS. 3 and 4.

Figure 3:
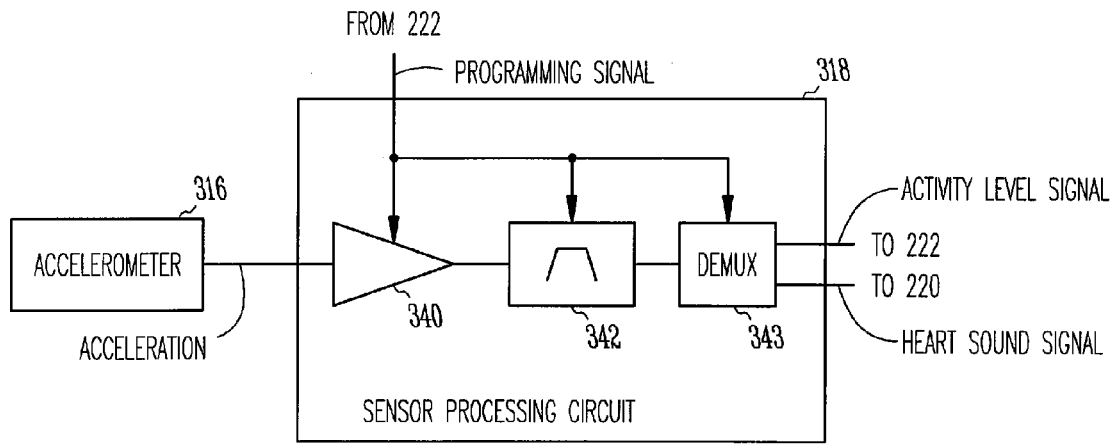
FIG. 3 is a block diagram illustrating an embodiment of a circuit including a dual-use sensor and a sensor processing circuit for sensing a physical activity level and a heart sound signal.

FIG. 3 is a block diagram illustrating an embodiment of a circuit including an accelerometer 316 for sensing the acceleration signal and a sensor processing circuit 318 for producing the activity level signal and the heart sound signal from the acceleration signal. Accelerometer 316 is one embodiment of dual-use sensor 216 or a portion thereof Sensor processing circuit 318 is one embodiment of sensor processing circuit 218 or a portion thereof.

Sensor processing circuit 318 includes an amplifier 340, a band-pass filter 342, and a demultiplexer (DEMUX) 343. It produces the activity level signal and the heart sound signal from the acceleration signal sense by accelerometer 316 on a time-sharing basis. During predetermined first time periods, sensor processing circuit 318 produces the activity level signal. During predetermined second time periods, sensor processing circuit 318 produces the heart sound signal. The first and second time periods do not overlap. Sensor processing circuit programming module 232 controls the first time periods for producing the activity level signal and the second time periods for producing the heart sound signal by programming the gain of amplifier 340, the cutoff frequencies of band-pass filter 342, and the connections within demultiplexer 343. Thus, sensor processing circuit 318 has an input to receive the acceleration signal, an output representative of the activity level signal during the first periods, and another output representative of the heart sound signal during the second periods. In one embodiment, the gain and/or the cutoff frequencies are predetermined and stored in memory circuit 224. In one specific embodiment, the gain and/or the cutoff frequencies are empirically determined based on data collected from the patient treated with system 100, and programmed into implantable medical device 110 by using external system 170. In one embodiment, the gain and/or the cutoff frequencies are adjustable by the user, when necessary, after the implantation of implantable medical device 110. The adjustments may become necessary when, for example, the range of the amplitude of the sensed acceleration signal has significantly changed, or when a different type of the heart sound is sought. Demultiplexer 343 receives the output of band-pass filter 342 and provides two outputs separately representing the activity level signal and the heart sound signal.

For producing the activity level signal, the gain of amplifier 340 is a first gain programmable in the range of 100 to 500. The cutoff frequencies of band-pass filter 342 are a first set of cutoff frequencies including a first low cutoff frequency programmable in a range of 0.5 Hz to 2 Hz and a first high cutoff frequency programmable in a range of 5 Hz to 15 Hz. In one specific embodiment, sensor processing circuit programming module 232 programs the first gain to 125, the first low cutoff frequency to 1 Hz, and the first high cutoff frequency to 10 Hz during the predetermined first time periods. For producing the heart sound signal, the gain of amplifier 340 is a second gain programmable in the range of 500 to 2000. The cutoff frequencies of band-pass filter 342 are a second set of cutoff frequencies including a second low cutoff frequency programmable in a range of 5 Hz to 10 Hz and a second high cutoff frequency programmable in a range of 50 Hz to 200 Hz. In one specific embodiment, sensor processing circuit programming module 232 programs the second gain to 1000, the second low cutoff frequency to 10 Hz, and the second high cutoff frequency to 100 Hz during the predetermined second time periods.

Sensor processing circuit 318 requires only one set of an amplifier and a filter to produce both the activity level signal and the heart sound signal. It is suitable for applications in which the activity level and the heart sounds need not be sensed concurrently. For an implantable pacemaker that already requires an accelerometer for the purpose of rate responsive pacing, sensor processing circuit 318 provides for heart sound sensing with minimal additional requirement for circuit size and energy consumption.

Figure 4:
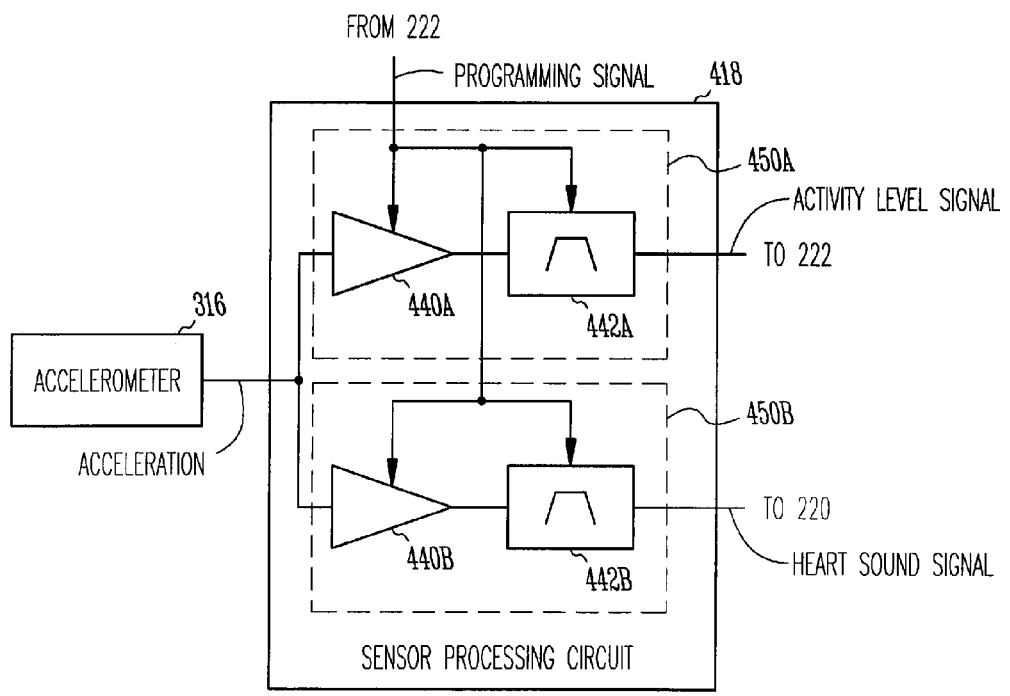
FIG. 4 is a block diagram illustrating another embodiment of the circuit including the dual-use sensor and the sensor processing circuit for sensing the physical activity level and the heart sound signal.

FIG. 4 is a block diagram illustrating another embodiment of the circuit including accelerometer 316 for sensing the acceleration signal and a sensor processing circuit 418 for concurrently producing the activity level signal and the heart sound signal from the acceleration signal. Accelerometer 316 is one embodiment of dual-use sensor 216 or a portion thereof. Sensor processing circuit 418 is one embodiment of sensor processing circuit 218 or a portion thereof.

Sensor processing circuit 418 includes a first processing circuit 450A for producing the activity level signal and a second processing circuit 450B for producing the heart sound signal. First processing circuit 450A includes a first amplifier 440A having a first gain and a first band-pass filter 442A having a first set of cutoff frequencies. Second processing circuit 450B includes a second amplifier 440B having a second gain and a second band-pass filter 442B having a second set of cutoff frequencies. First processing circuit 450A and second processing circuit 450B operate in parallel to allow concurrent sensing of the physical activity level and the heart sounds. Thus, sensor processing circuit 418 has an input to receive the acceleration signal, an output representative of the activity level signal, and another output representative of the heart sound signal. In one embodiment, the gains and/or the cutoffs frequencies are predetermined and stored in memory circuit 224. While there is no need to program the gains and the cutoff frequencies for the time-sharing purpose, in one embodiment, the gains and/or the cutoffs frequencies are programmable to ensure proper sensing under each patient's particular circumstances. In one embodiment, the gain and/or the cutoff frequencies are empirically determined based on data collected from the patient, and programmed into implantable medical device 110 by using external system 170. In one embodiment, the gain and/or the cutoff frequencies are adjustable by the user, when necessary, after the implantation of implantable medical device 110.

The gain of amplifier 440A (the first gain) is programmable in the range of 100 to 500. The cutoff frequencies of band-pass filter 442A (the first set of cutoff frequencies) include a first low cutoff frequency programmable in a range of 0.5 Hz to 2 Hz and a first high cutoff frequency programmable in a range of 5 Hz to 15 Hz. In one specific embodiment, sensor processing circuit programming module 232 programs the first gain to 125, the first low cutoff frequency to 1 Hz, and the first high cutoff frequency to 10 Hz during the predetermined first time periods. The gain of amplifier 440B (the second gain) is programmable in the range of 500 to 2000. The cutoff frequencies of band-pass filter 442B (the second set of cutoff frequencies) include a second low cutoff frequency programmable in a range of 5 Hz to 10 Hz and a second high cutoff frequency programmable in a range of 50 Hz to 200 Hz. In one specific embodiment, sensor processing circuit programming module 232 programs the second gain to 1000, the second low cutoff frequency to 10 Hz, and the second high cutoff frequency to 100 Hz during the predetermined second time periods.

Sensor processing circuit 418 allows concurrent sensing of the activity level and the heart sounds. With sensor processing circuit 418, dual-use sensor 216 is usable for sensing the activity level and the heart sounds simultaneously when needed.

Figure 5A:
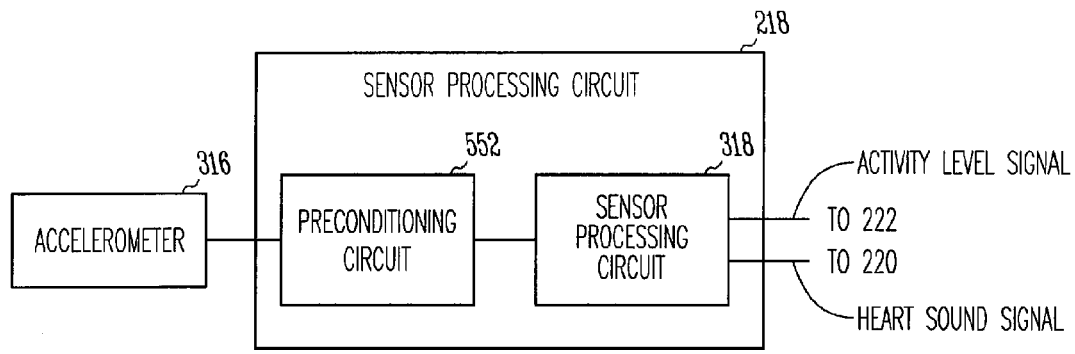
FIG. 5A is a block diagram illustrating an embodiment of the circuit of FIG. 3 in which the sensor processing circuit includes an additional preconditioning circuit.

FIG. 5A is a block diagram illustrating an embodiment of the circuit of FIG. 3 with an additional preconditioning circuit 552. In this embodiment, sensor processing circuit 218 includes preconditioning circuit 552 with its input connected to accelerometer 316 and its output connected to sensor processing circuit 318.

Figure 5B:
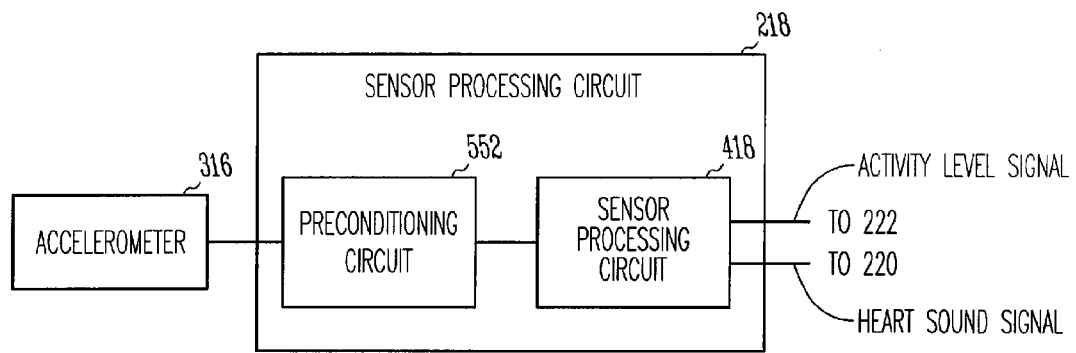
FIG. 5B is a block diagram illustrating an embodiment of the circuit of FIG. 4 in which the sensor processing circuit includes an additional preconditioning circuit.

FIG. 5B is a block diagram illustrating an embodiment of the circuit of FIG. 4 with an additional preconditioning circuit 552. In this embodiment, sensor processing circuit 218 includes preconditioning circuit 552 with its input connected to accelerometer 316 and its output connected to sensor processing circuit 418.

Figure 5C:
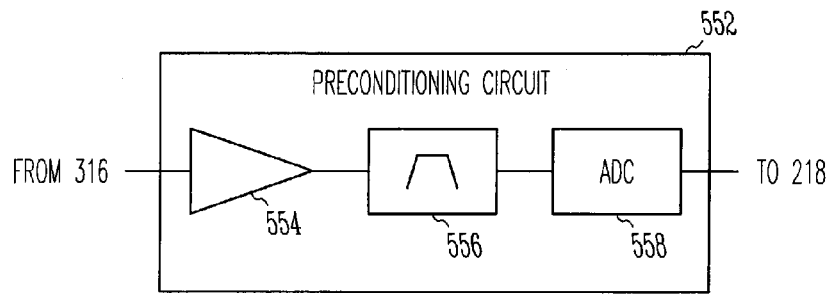
FIG. 5C is a block diagram illustrating an embodiment of a circuit of the additional preconditioning circuit.

FIG. 5C is a block diagram illustrating an embodiment of a circuit of preconditioning circuit 552. Preconditioning circuit 552 provides for initial conditioning or processing of the acceleration signal before being processed for producing the activity level signal and the heart sound signal.

In one embodiment, preconditioning circuit 552 includes a preconditioning amplifier 554 having a preconditioning gain and a preconditioning band-pass filter 556 having a set of preconditioning cutoff frequencies. In one embodiment, the preconditioning gain is programmable in the range of 100 to 500. The overall gains for producing the activity signal and the heart sound signal are products of the preconditioning gain (gain of preconditioning amplifier 554) multiplied by the gains of sensor processing circuit 318 or 418 as discussed above. The gains to be programmed to sensor processing circuit 318 or 418 are calculated by dividing the gains discussed above by the programmed preconditioning gain. That is, the gain of amplifier 340 includes a first gain in the range of 100 to 500 divided by the preconditioning gain for producing the activity signal, and a second gain in the range of 500 to 2000 divided by the preconditioning gain for producing the heart sound signal. The gain of amplifier 440A (the first gain) is in the range of 100 to 500 divided by the preconditioning gain. The gain of amplifier 440B (the second gain) is in the range of 500 to 2000 divided by the preconditioning gain. In one embodiment, the set of preconditioning cutoff frequencies includes a low preconditioning cutoff frequency programmable in the range of 0.5 to 2 Hz, and a high preconditioning cutoff frequency programmable in the range of 50 to 200 Hz. In one specific embodiment, with sensor processing circuit 318, the preconditioning gain is 125, the low preconditioning cutoff frequency is 1 Hz, the high preconditioning cutoff frequency programmable is 100 Hz, the first gain for amplifier 340 is 1, and the second gain for amplifier 340 is 8. In an alternative specific embodiment, with sensor processing circuit 418, the preconditioning gain is 125, the low preconditioning cutoff frequency is 1 Hz, the high preconditioning cutoff frequency programmable is 100 Hz, the gain for amplifier 440A is 1, and the gain for amplifier 440B is 8.

In one embodiment, preconditioning circuit 552 further includes an analog-to-digital converter (ADC) 558 to digitize the acceleration signal. This allows sensor processing circuit 318 or sensor processing circuit 418 to be implemented with digital technology. That is, the activity level signal and the heart sound signal are digital signals produced from the digitized acceleration signal using digital signal processing. In one embodiment, ADC 558 has a programmable sampling rate, and implantable controller 222 includes a digitization control module to control this sampling rate. In one further embodiment, the sampling rate is programmable through external system 170. In general, sensor processing circuit 218 can be implemented with hardware, software, and a combination of both.

Figure 6:
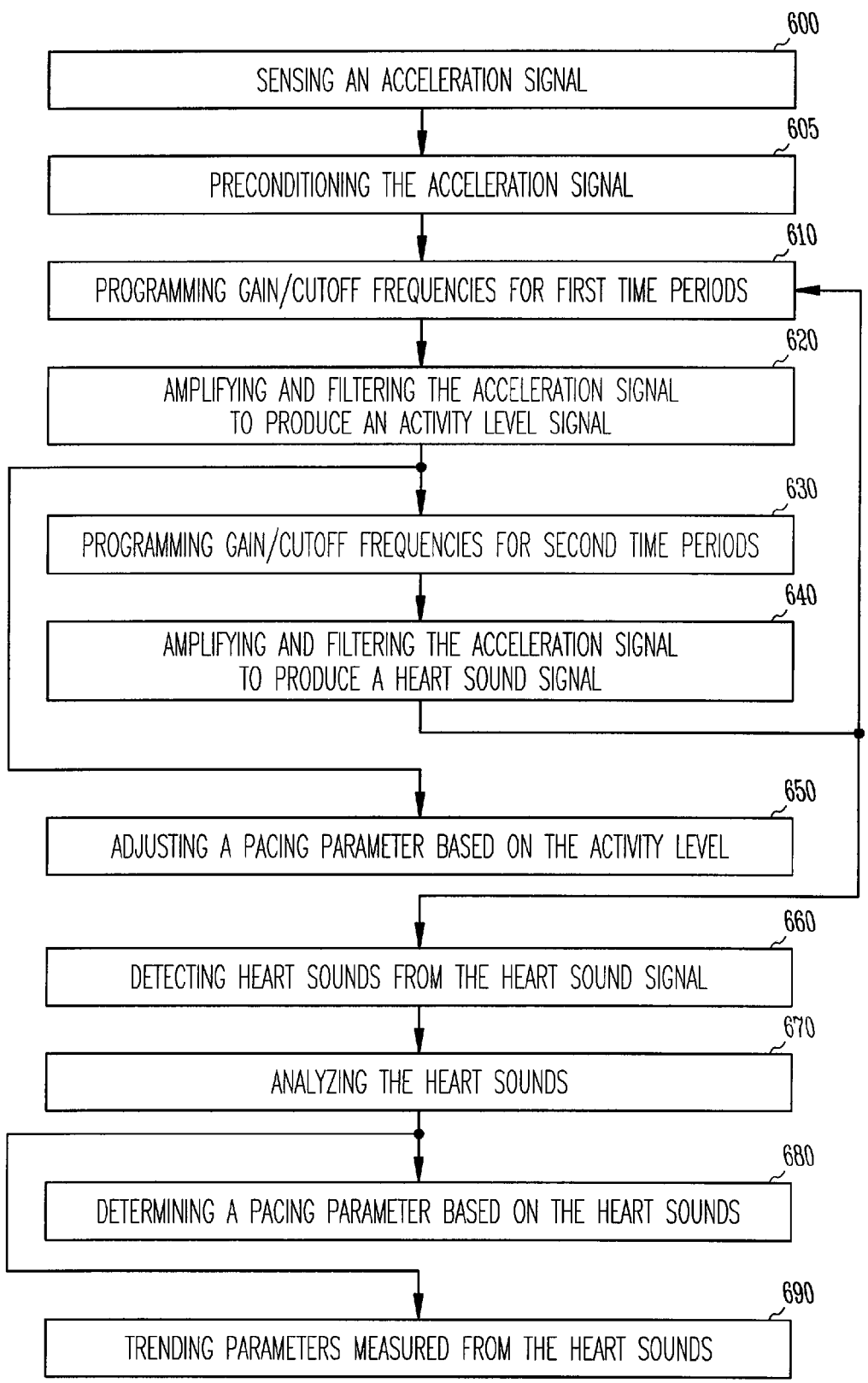
FIG. 6 is a flow chart illustrating an embodiment of a method for sensing the physical activity level and the heart sounds by using the circuit of FIGS. 3 and 5.

FIG. 6 is a flow chart illustrating an embodiment of a method for sensing the physical activity level and the heart sounds with the circuit illustrated in FIGS. 3 and 5. The method illustrates by way of example, but not by way of limitation, a use of the circuit that includes accelerometer 316, preconditioning circuit 552, and sensor processing circuit 318.

Accelerometer 316 senses an acceleration signal at 600. Preconditioning circuit 552 preconditions the sensed acceleration signal at 605. In one embodiment, preconditioning circuit 552 amplifies and filters the sensed acceleration signal. In a further embodiment, preconditioning circuit 552 digitizes the sensed acceleration signal. The digitization allows subsequent processing to be performed using digital signal processing technology.

Sensor processing circuit 318 is programmed with the first gain and the first set of cutoff frequencies for first time periods at 610. During the first time periods, sensor processing circuit 318 amplifies and filters the acceleration signal to produce the activity level signal at 620. Sensor processing circuit 318 is programmed with the second gain and the second set of cutoff frequencies for second time periods at 630. During the second time periods, sensor processing circuit 318 amplifies and filters the acceleration signal to produce the heart sound signal at 640. In one embodiment, the first and second time periods are programmed into memory circuit 224 for use by sensor processing circuit programming module 232, which programs the gain and the cutoff frequencies of sensor processing circuit 318. The first and second time periods do not overlap.

Rate responsive pacing algorithm execution module 230 adjusts a pacing parameter such as the pacing interval based on at least the activity level signal at 650. In one embodiment, rate responsive pacing algorithm execution module 230 also adjusts the pacing interval and/or one or more other pacing parameters based on other signals such as the electrograms and the heart sound signal.

Heart sounds are detected from the heart sound at 660. In one embodiment, heart sound detector 220, which is a part of implantable medical device 110, detects the heart sounds from the heart sound signal. In one embodiment, the detected hearts sounds are used by implant controller 222 for pacing control purposes. In another embodiment, the heart sound signal and/or information extracted from the detected heart sounds are transmitted to external system 170. In an alternative embodiment, the heart sound signal is transmitted to external system 170, which includes a heart sound detector to detect the heart sounds. The heart sound detection includes detection of predetermined types of heart sounds including one or more of S1, S2, S3, and S4. The heart sounds are analyzed at 670. The analysis includes measurement of, for example, one or more of amplitude of any type heart sound, relative amplitude between any two types of heart sounds, duration of each type heart sound, interval between any type or types of heart sounds, interval between any type heart sound and any type electrical event of the heart, fundamental frequency of each type heart sound, and harmonic frequency of each type heart sound. In one embodiment, the results of the analysis, such as parameters generated from the above measurements, are used to determine a pacing parameter based on the heart sounds at 680. One example of determining a pacing parameter based on the heart sounds is discussed in U.S. patent application Ser. No. 10/307,896. In one embodiment, one or more parameters generated from the above measurements are trended at 690. One example of trending heart sound related parameters is discussed in U.S. patent application Ser. No. 10/334,694.

Figure 7:
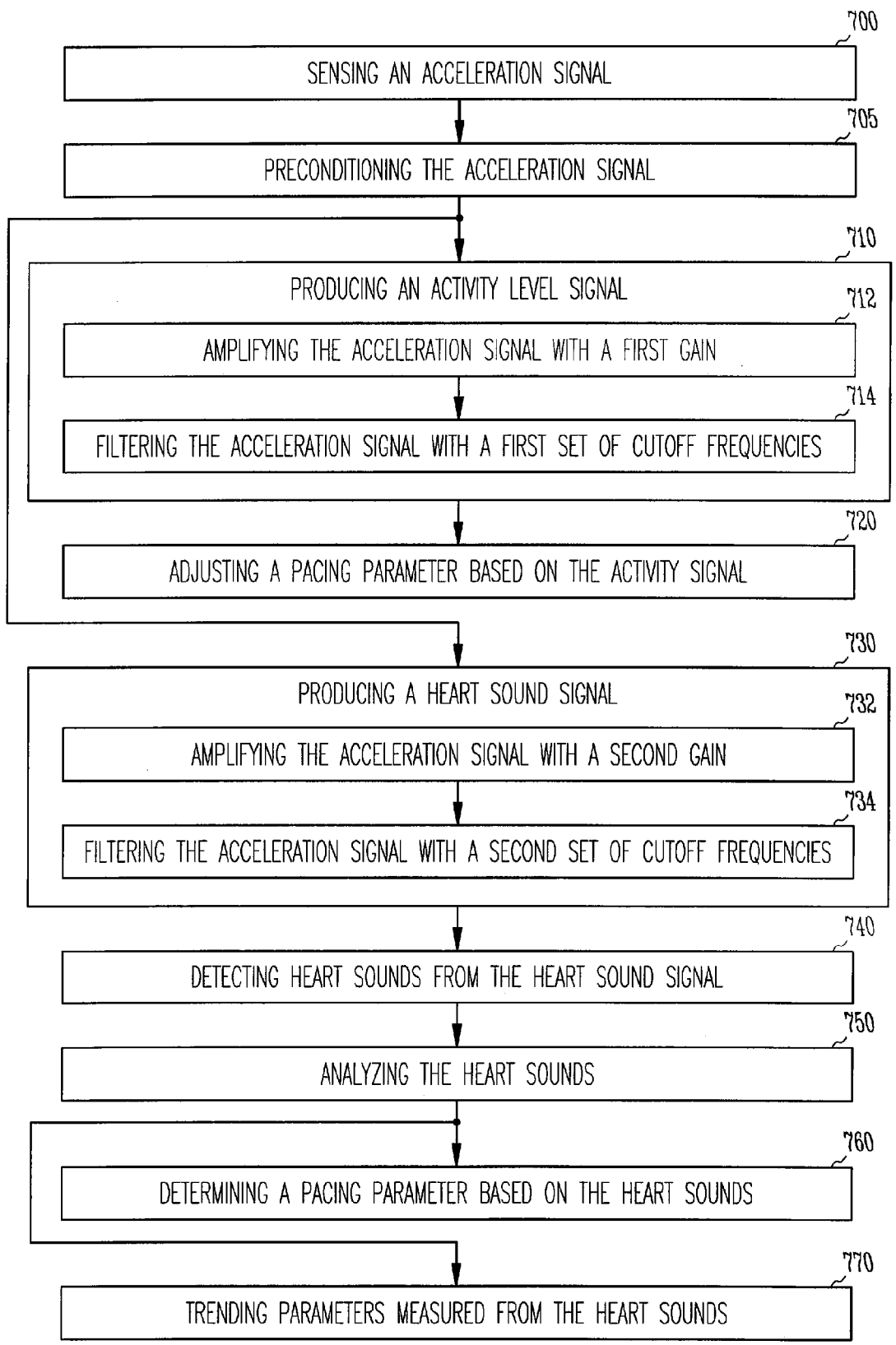
FIG. 7 is a flow chart illustrating an embodiment of a method for sensing the physical activity level and the heart sounds by using the circuit of FIGS. 4 and 5.

FIG. 7 is a flow chart illustrating an embodiment of a method for sensing the physical activity level and the heart sounds with the circuit illustrated in FIGS. 4 and 5. The method illustrates by way of example, but not by way of limitation, a use of the circuit that includes accelerometer 316, preconditioning circuit 552, and sensor processing circuit 418.

Accelerometer 316 senses an acceleration signal at 700. Preconditioning circuit 552 preconditions the sensed acceleration signal at 705. In one embodiment, preconditioning circuit 552 amplifies and filters the sensed acceleration signal. In a further embodiment, preconditioning circuit 552 digitizes the sensed acceleration signal. The digitization allows subsequent processing to be performed using digital signal processing technology.

First processing circuit 450A of sensor processing circuit 418 produces the activity level signal from the acceleration signal at 710. This includes amplifying the acceleration signal with the first gain at 712 and filtering the acceleration signal with the first set of cutoff frequencies at 714. Rate responsive pacing algorithm execution module 230 adjusts a pacing parameter such as the pacing interval based on the activity level signal at 720. In one embodiment, rate responsive pacing algorithm execution module 230 also adjusts the pacing interval and/or one or more other pacing parameters based on other signals such as the electrograms and the heart sound signal.

Second processing circuit 450B of sensor processing circuit 418 produces the heart sound signal from the acceleration signal at 730. This includes amplifying the acceleration signal with the second gain at 732 and filtering the acceleration signal with the second set of cutoff frequencies at 734. Heart sounds are detected from the heart sound signal at 740 and analyzed at 750. In one embodiment, the results of the analysis are used to determine a pacing parameter based on the heart sounds at 760. In one embodiment, the results of the analysis are used for trending one or more parameters measured from the heart sounds at 770. In one embodiment, step 660 is identical or similar to step 740, step 670 is identical or similar to step 750, step 680 is identical or similar to step 760, and step 690 is identical or similar to step 770.

Because first processing circuit 450A and second processing circuit 450B are separate circuits producing distinguished signals from a common signal, step 710 (and its subsequent step 720) and step 730 (and its subsequent steps 740, 750, 760, and 770) can be performed concurrently.

It is to be understood that the above detailed description is intended to be illustrative, and not restrictive. For example, the sensor processing circuit can be expanded to produce additional signals from the acceleration signal, such as a respiration-indicative signal, if the additional signals each have a distinguishable spectrum. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An implantable medical device, comprising:
    a sensing circuit configured to sense at least one electrogram;
    a pacing circuit configured to deliver pacing pulses;
    a dual-use sensor configured to sense a signal indicative of physical activities and heart sounds;
    a preconditioning circuit configured to precondition the sensed signal, the preconditioning circuit including a preconditioning amplifier having a preconditioning gain, a preconditioning band-pass filter having a set of preconditioning cutoff frequencies, and an analog-to-digital converter (ADC) to produce the preconditioned sensed signal by amplifying, filtering, and digitizing the sensed signal;
    a sensor processing circuit configured to produce an activity level signal and a heart sound signal using the preconditioned sensed signal, the activity level signal indicative of a level of the physical activities, the heart sound signal indicative of the heart sounds, the sensor processing circuit including:
        a first set of cutoff frequencies suitable for producing the activity level signal;
        a first gain suitable for producing the activity level signal;
        a second set of cutoff frequencies suitable for producing the heart sound signal; and
        a second gain suitable for producing the heart sound signal;
    an implant controller coupled to the sensing circuit, the pacing circuit, and the sensor processing circuit, the controller configured to control the delivery of the pacing pulses using the activity level signal and the heart sound signal; and
    an implantable housing encapsulating at least the sensing circuit, the pacing circuit, the sensor processing circuit, and the controller.

2. The device of claim 1, wherein the dual-use sensor is a single integrated circuit accelerometer.

3. The device of claim 1, wherein the sensor processing circuit is configured to produce the activity level signal during a first time period and the heart sound signal during a second time period, wherein the first time period and the second time period do not overlap.

4. The device of claim 3, wherein the implant controller comprises a sensor processing circuit programming module configured to program the sensor processing circuit for producing the activity level signal using the first set of cutoff frequencies and the first gain during a first time period and producing the heart sound signal using the second set of cutoff frequencies and the second gain during a second time period.

5. The device of claim 4, wherein the sensor processing circuit comprises:
    a band-pass filter having programmable cutoff frequencies; and
    an amplifier having a programmable gain,
        wherein the programmable cutoff frequencies and the programmable gain are adjustable after implantation of the implantable medical device.

6. The device of claim 1, wherein the sensor processing circuit is configured to produce the activity level signal and the heart sound signal concurrently.

7. The device of claim 6, wherein the sensor processing circuit comprises:
    a first band-pass filter having the first set of cutoff frequencies;
    a first amplifier having the first gain;
    a second band-pass filter having the second set of cutoff frequencies; and
    a second amplifier having the second gain.

8. The device of claim 7, wherein the first band-pass filter has a first set of programmable cutoff frequencies, and the second band-pass filter has a second set of programmable cutoff frequencies.

9. The device of claim 7, wherein the first amplifier having a first programmable gain, and the second amplifier has a second programmable gain.

10. The method for operating an implantable medical device, the method comprising:
   sensing a signal indicative of physical activities and heart sounds using a single implantable sensor;
   preconditioning the sensed signal, the preconditioning including amplifying, filtering, and digitizing the sensed signal using a preconditioning circuit of the implantable medical device;
   producing an activity level signal by filtering the preconditioned sensed signal using first cutoff frequencies and amplifying the preconditioned sensed signal using a first gain;
   producing a heart sound signal by filtering the preconditioned sensed signal using second cutoff frequencies and amplifying the preconditioned sensed signal using a second gain; and
   controlling delivery of cardiac pacing pulses from the implantable medical device using the activity level signal and the heart sound signal.

11. The method of claim 10, wherein sensing the signal comprises sensing an acceleration signal using an implantable accelerometer.

12. The method of claim 10, comprising:
   producing the activity level signal during a first time period; and
producing the heart sound signal during a second time period, wherein the first time period and the second time period do not overlap.

13. The method of claim 12, comprising producing the activity level signal and the heart sound signal using a band-pass filter having programmable cutoff frequencies and an amplifier having a programmable gain, wherein producing the activity level signal comprises:
   programming the programmable cutoff frequencies to the first cutoff frequencies for the first time period; and
   programming the programmable gain to the first gain for the first time period,
   and producing the heart sound signal comprises:
   programming the programmable cutoff frequencies to the second cutoff frequencies for the second time period; and
   programming the programmable gain to the second gain for the second time period.

14. The method of claim 10, comprising producing the activity level signal and the heart sound signal concurrently.

15. The method of claim 14, comprising:
   producing the activity level signal using a first band-pass filter having the first cutoff frequencies and a first amplifier having the first gain; and
   producing the activity level signal using a second band-pass filter having the second cutoff frequencies and a second amplifier having the second gain.

16. An implantable medical device, comprising:
   means for sensing a signal indicative of physical activities and heart sounds using a single implantable sensor;
   means for preconditioning the sensed signal, including means for amplifying, filtering, and digitizing the sensed signal; and
   means for controlling gains and cutoff frequencies for producing an activity level signal and a heart sound signal using the preconditioned sensed signal.

17. The device of claim 16, comprising means for controlling cardiac pacing using one or more of the activity level signal and the heart sound signal.

18. The device of claim 17, wherein the means for controlling cardiac pacing comprise means for determining one or more pacing parameters using the one or more of the activity level signal and the heart sound signal.

19. The device of claim 18, wherein the means for controlling gains and cutoff frequencies comprises means for controlling gains and cutoff frequencies for producing the activity level signal and the heart sound signal concurrently.

20. The device of claim 18, wherein the means for controlling gains and cutoff frequencies comprises means for controlling gains and cutoff frequencies for producing the activity level signal during a first time period and producing the heart sound signal during a second time period, wherein the first time period and the second time period do not overlap.

* * * * *